United States Patent [19]
Bandman et al.

[11] Patent Number: 6,162,601
[45] Date of Patent: Dec. 19, 2000

[54] HUMAN PININ SPLICE VARIANT

[75] Inventors: Olga Bandman, Mountain View; Preeti Lal; Purvi Shah, both of Sunnyvale, all of Calif.

[73] Assignee: Incyte Pharmaceuticals, Inc., Palo Alto, Calif.

[21] Appl. No.: 08/910,925

[22] Filed: Aug. 8, 1997

[51] Int. Cl.[7] .............................. C12Q 1/68; C12N 15/85; C12N 5/10; C07H 21/04

[52] U.S. Cl. .............................. 435/6; 435/325; 435/366; 435/320.1; 435/69.1; 435/91.1; 435/91.2; 536/23.1; 536/23.5

[58] Field of Search ..................................... 435/325, 366, 435/320.1, 69.1, 6, 91.1, 91.2; 536/23.1, 23.5, 24.3

[56] References Cited

PUBLICATIONS

Duo et al., GenBank Accession No. U59479, Jul. 1996.

Finbow, M.E. et al., "Ductin—a proton pump component, a gap junction channel and a neurotramsmitter release channel", *BioEssays,* 17: 247–255 (1995).

Ouyang, P. and S.P. Sugrue, "Characterization of Pinin, A Novel Protein Associated with the Desmosome–Intermediate Filament Complex", *J. Cell Biol.,* 135: 1027–1042 (1996) (GI 1684842; GI 1684843; GI 1684846; GI 1684847).

Krawczyk, W.S. and G.F. Wilgram, "Hemidesmosome and Desmosome Morphogenesis during Epidermal Wound Healing", *J. Ultrastructure Res.*, 45: 93–101 (1973).

Plotnick, H. and A. Lupulescu, "Ultrastructural studies of xeroderma pigmentosum", *J. Am. Acad. Dermatol.,* 9: 876–882 (1983).

Wegiel, J. and H.M. Wisniewski, "Rosenthal fibers, eosinophilic inclusions, and anchorage densities with desmosome–like structures in astrocytes in Alzheimer's disease", *Acta Neuropathol.*, 87: 355–361 (1994).

Sepp, R. et al., "Altered patterns of cardiac intercellular junction distribution in hypertrophic cardiomyopathy", *Heart,* 76: 412–417 (1996).

Cooley, J.E. et al., "Hailey–Hailey Disease Keratinocytes: Normal Assembly of Cell–Cell Junctions In Virto", *J. Invest. Dermatol.*, 107: 877–881 (1996).

Imai, Y. and M. Yamakawa, "Morphology, function and pathology of follicular dendritic cells", *Pathol. Int.*, 46: 807–833 (1996).

Witkop, Jr., C.J. et al., "Hereditary Mucoepithelial Dysplasia: A Disease Apparently of Desmosome and Gap Junction Formation", *Am. J. Hum. Genet.*, 31: 414–427 (1979).

Suster, S. and C.A. Moran, "Chordomas of the Mediastinum: Clinicopathologic, Immunohistochemical, and Utrastructural Study of Six Cases Presenting as Posterior Mediastinal Masses", *Hum. Pathol.*, 26: 1354–1362 (1995).

Mrak, R.E. and G.F. Baker, "Granular cell basal cell carcinoma", *J. Cutan. Pathol.*, 14: 37–42 (1987).

Sugrue, S.P. and P. Ouyang, (Direct Submission), GenBank Sequence Database (Acession U77717), National Center for Biotechnology Information, National Library of Medicine, Bethesda, Maryland, 20894 (GI 1684842; GI 1684843).

Franke, W.W. et al., "Isolation and symmetrical splitting of desmosomal structuresin 9 M urea", *Eur. J. cell Biol,* 32: 117–130 (1983).

Stillwell, W. and K. Doram, "Measurement of Transmembrane Proton Diffusion Using Two Liposome–Sequestered pH Indicator Dyes", *Biochem. Biophys. Res. Comm.*, 93: 326–332 (1980).

*Primary Examiner*—David Guzo
*Attorney, Agent, or Firm*—Incyte Genomics, Inc.

[57] ABSTRACT

The invention provides a human pinin splice variant (PNIN) and polynucleotides which identify and encode PNIN. The invention also provides expression vectors, host cells, agonists, antibodies and antagonists. The invention also provides methods for treating disorders associated with expression of PNIN.

9 Claims, 12 Drawing Sheets

FIGURE 1A

```
5' TCT CAA GCC            TGC CGC AGG            GAG AAG ATG            GCG GTC AGA            ACT TTG CAG            GAA
                                                          9                    18                    27                    36                    45                    54
                                                                                    M   A   V   R   T   L   Q   E

CAG CTG GAA            AAG GCC AGT            GAG AGT CTT            AAG AAC GTG            GAT GAG AAT            ATT CGC AAG
                                63                    72                    81                    90                    99                   108
   Q   L   E              K   A   S              E   S   L              K   N   V              D   E   N              I   R   K

CTC ACC GGG            CGG GAT CCG            AAT GAC GTG            AGG CCC ATC            CAA GCC AGA            TTG CTG GCC
                               117                   126                   135                   144                   153                   162
   L   T   G              R   D   P              N   D   V              R   P   I              Q   A   R              L   L   A

CTT TCT GGT            CCT GGA GGT            AGA GGA CGT            GGT AGT TTA            TTA CTG AGG            CGT GGA
                               171                   180                   189                   198                   207                   216
   L   S   G              P   G   G              R   G   R              G   S   L              L   L   R              R   G

TTC TCA GAT            AGT GGA GGA            CCC AAA CCA            GCC AGA GAC            CTT GAA GGG            GCA
                               225                   234                   243                   252                   261                   270
   F   S   D              S   G   G              P   K   P              A   R   D              L   E   G              A

GTC AGT AGG            GGG CTG GGC            GAG CGT CGG            ACC AGA AGA            TCA CGC CAG            GAA AGC
                               279                   288                   297                   306                   315                   324
   V   S   R              G   L   G              E   R   R              T   R   R              S   R   Q              E   S

GAC CCG GAG            GAT GAT GAT            AAG CCA GCA            TTG CAG TCT            TCA GTT GTA            GCT
                               333                   342                   351                   360                   369                   378
   D   P   E              D   D   D              K   P   A              L   Q   S              S   V   V              A
```

```
      387         396         405         414         423         432
ACC TCC AAA GAG CGC ACA CGT AGA GAC CTT ATC CAG GAT CAA AAT ATG GAT GAA
 T   S   K   E   R   T   R   R   D   L   I   Q   D   Q   N   M   D   E 441         450         459         468         477         486
AAG GGA AAG CAA AGG AAC CGG CGA ATA TTT GGC TTG TTG ATG GGT ACC CTT CAA
 K   G   K   Q   R   N   R   R   I   F   G   L   L   M   G   T   L   Q 495         504         513         522         531         540
AAA TTT AAA CAA GAA TCC ACT GTT CAG GCT ACT GAA AGG CAA CGG CGC CAG GAA
 K   F   K   Q   E   S   T   V   Q   A   T   E   R   Q   R   R   Q   E 549         558         567         576         585         594
ATT GAA CAA AAA CTT GAA GTT CAG GCA GAA GAG AGA AAG CAG GTT GAA AAT
 I   E   Q   K   L   E   V   Q   A   E   E   R   K   Q   V   E   N 603         612         621         630         639         648
GAA AGG GAA CTG TTT GAA GAG AGG CGT GCT AAA CAG ACA GAA CTG CGG CTT
 E   R   E   L   F   E   E   R   R   A   K   Q   T   E   L   R   L 657         666         675         684         693         702
TTG CAG AAA GTT GAG CTT GCG CAG CTG CAA GAA GAA TGG AAT GAA CAT AAT
 L   Q   K   V   E   L   A   Q   L   Q   E   E   W   N   E   H   N 711         720         729         738         747         756
GCC AAA ATA ATT AAA TAT ATA AGA ACT AAG ACA AAG CCC CAT TTG TTT TAT ATT
 A   K   I   I   K   Y   I   R   T   K   T   K   P   H   L   F   Y   I
```

FIGURE 1B

```
         765                774              783                 792            801             810
CCT GGA AGA ATG TGT CCA GCT ACC CAA AAA CTA ATA GAA GAG TCA CAG AGA AAA
 P   G   R   M   C   P   A   T   Q   K   L   I   E   E   S   Q   R   K 819                828              837                 846            855             864
ATG AAC GCT TTA TTT GAA GGT AGA CGC ATC GAA TTT GCA GAA ATA AAT AAA
 M   N   A   L   F   E   G   R   R   I   E   F   A   E   I   N   K 873                882              891                 900            909             918
ATG GAG GCT AGG CCT AGA AGA CAA TCA ATG AAG GAA AAA GAG CAT CAG GTG GTG
 M   E   A   R   P   R   R   Q   S   M   K   E   K   E   H   Q   V   V 927                936              945                 954            963             972
CGT AAT GAA CAG AGA AGA CAA AAG GCG GAA GAG CAA GAG GAG AAG GTG GCT CAG CGA GAG
 R   N   E   Q   R   R   Q   K   A   E   E   Q   E   E   K   V   A   Q   R   E 981                990              999                 1008           1017            1026
GAA GAG TTG GAG GAG GAG ACA GGT AAT CAG CAC AAT GAT GTA GAA ATA GAG GAA GCA
 E   E   L   E   E   E   T   G   N   Q   H   N   D   V   E   I   E   E   A 1035               1044             1053                1062           1071            1080
GGA GAA GAA GAA GAA AAG GAA ATA GCG ATT GTT CAT AGT GAT GCA GAG AAA GAA
 G   E   E   E   E   K   E   I   A   I   V   H   S   D   A   E   K   E 1089               1098             1107                1116           1125            1134
CAG GAG GAA GAA CAA AAA CAG GAA ATG GAG GTT AAG ATG GAG GAA ACT
 Q   E   E   E   Q   K   Q   E   M   E   V   K   M   E   E   T
```

FIGURE 1C

```
      1143            1152            1161            1170            1179            1188
GAG GTA AGG GAA AGT GAG AAG CAG CAG GAT AGT CAG CCT GAA GAA GTT ATG GAT
 E   V   R   E   S   E   K   Q   Q   D   S   Q   P   E   E   V   M   D 1197            1206            1215            1224            1233            1242
GTG CTA GAG ATG GTT GAG AAT GTC AAA CAT GTA ATT GCT GAC CAG GAG GTA ATG
 V   L   E   M   V   E   N   V   K   H   V   I   A   D   Q   E   V   M 1251            1260            1269            1278            1287            1296
GAA ACT AAT CGA GTT GAA AGT GTA GAA CCT TCA GAA AAT GAA GCT AGC AAA GAA
 E   T   N   R   V   E   S   V   E   P   S   E   N   E   A   S   K   E 1305            1314            1323            1332            1341            1350
TTG GAA CCA GAA ATG GAA TTT GAA ATT GAG CCA GAT AAA GAA AAG GAG TCT CTT
 L   E   P   E   M   E   F   E   I   E   P   D   K   E   K   E   S   L 1359            1368            1377            1386            1395            1404
TCT CCT GGG AAA GAA AAT GTC AGT GCT TTA GAC ATG GAA ATG GAA TGT GAG GAA
 S   P   G   K   E   N   V   S   A   L   D   M   E   M   E   C   E   E 1413            1422            1431            1440            1449            1458
AAA GAA AAA GAA TCT CAA CCC GAG CCT GAG CCT CAA CCT GTG GCT CAA CCT CCT
 K   E   K   E   S   Q   P   E   P   E   P   Q   P   V   A   Q   P   P 1467            1476            1485            1494            1503            1512
CAG TCT CAG CCC CAG CTT CAA TCC CAG TCC CAA TCC CAA CTT CAG CTC CAG TCC
 Q   S   Q   P   Q   L   Q   S   Q   S   Q   S   Q   P   V   L   Q   S

FIGURE 1D
```

```
          1521          1530          1539          1548          1557          1566
CAG CCT CCC TCT CAG CCT GAG GAT TCA TTA GCT GTT TTA CAG CCA ACA CCC
 Q   P   P   S   Q   P   E   D   L   S   L   A   V   L   Q   P   T   P 1575          1584          1593          1602          1611          1620
CAA GTT ACT CAG GAG CAA GGG CAT TTA CTA CCT GAG AGG AAG GAT TTT CCT GTA
 Q   V   T   Q   E   Q   G   H   L   L   P   E   R   K   D   F   P   V 1629          1638          1647          1656          1665          1674
GAG TCT GTA AAA CTC ACT GAG GTA CCA GTA GAG CCA GTC TTG ACA GTA CAT CCA
 E   S   V   K   L   T   E   V   P   V   E   P   V   L   T   V   H   P 1683          1692          1701          1710          1719          1728
GAG AAG AGC AAA ACC AAA ACT AGG AGC AGA AGT AGA GGT CGA GCT AGA AAT
 E   S   K   S   K   T   K   T   R   S   R   S   R   G   R   A   R   N 1737          1746          1755          1764          1773          1782
AAA ACA AGC AAG AGT AGC AGC CGA AGT AGC AGT AGA GGT TCT AGT AGC AGT
 K   T   S   K   S   S   S   R   S   S   S   R   G   S   S   S   S 1791          1800          1809          1818          1827          1836
TCA ACC AGT AGC AGT AGT GGA AGT AGT TCC AGC AGT GGA AGT AGC AGT CGC
 S   T   S   S   S   S   G   S   S   S   S   S   G   S   S   S   R 1845          1854          1863          1872          1881          1890
AGT AGT TCC AGC AGC TCC AGT ACA GGT GGC AGC AGC AGC AGA GAT AGT AGC
 S   S   S   S   S   S   S   T   G   G   S   S   S   R   D   S   S
```

FIGURE 1E

```
      1899      1908      1917      1926      1935      1944
AGT AGC ACT AGT AGT AGT GAG AGT AGA AGT CGG AGT AGG GGC CGG GGA CAT
 S   S   T   S   S   S   E   S   R   S   R   S   R   G   R   G   H 1953      1962      1971      1980      1989      1998
AAT AGA GAT AGA AAG CAC AGA AGG AGC GTG GAT CGG AAG AGA AGG GAT ACT TCA
 N   R   D   R   K   H   R   R   S   V   D   R   K   R   R   D   T   S 2007      2016      2025      2034      2043      2052
GGA CTA GAA AGA AGT CAC AAA TCT TCA AAA GGT AGT AGT AGA GAT ACA AAA
 G   L   E   R   S   H   K   S   S   K   G   S   S   R   D   T   K 2061      2070      2079      2088      2097      2106
GGA TCA AAG GAT AAG AAT TCC CGG TCC GAC AGA AAG AGG TCT ATA TCA GAG AGT
 G   S   K   D   K   N   S   R   S   D   R   K   R   S   I   S   E   S 2115      2124      2133      2142      2151      2160
AGT CGA TCA GGC AAA AGA TCT TCA AGA AGT GAA AGA GAC CGA AAA TCA GAC AGG
 S   R   S   G   K   R   S   S   R   S   E   R   D   R   K   S   D   R 2169      2178      2187      2196      2205      2214
AAA GAC AAA AGG CGT TAA TGG AAG AAG CCA GGC TTT CTT AGC CAT TCT TTG CAG
 K   D   K   R   R   *

2223      2232      2241      2250      2259      2268
CAG AAG ATT TCT TGA TAA AAA AGG ATT ACC TTT CCT TGT AAA GAG GAT GCT GCC
```

FIGURE 1F

```
       2277          2286           2295          2304           2313          2322
TTA AGA ATT GCA TGT TGT AAA AAA TCT TTT TGG AAA ATA CAG ACT GTT TGT TTA 2331          2340           2349          2358           2367
CCA GAC ATT CTT GTA CTT TTT GCA TAA TTT TGT AAG AGT TAT TTA TC 3'
```

FIGURE 1G

| | | |
|---|---|---|
| 1 | M A V A V R T L Q E Q L E K A K E S L K | 53219 |
| 1 | M A V A V R T L Q E Q L E K A K E S L K | GI 1684847 |
| 1 | M A V A V R T L Q E Q L E K A K E S L K | GI 1684843 |
| 21 | N V D E N I R K L T G R D P N D V R P I | 53219 |
| 21 | N V D E N I R K L T G R D P N D V R P I | GI 1684847 |
| 21 | N V D E N I R K L T G R D P N D V R P I | GI 1684843 |
| 41 | Q A R L L A L S G P G G G R G R G S L L | 53219 |
| 41 | Q A R L L A L S G P G G G R G R G S L L | GI 1684847 |
| 41 | Q A R L L A L S G P G G G R G R G S L L | GI 1684843 |
| 61 | L R R G F S D S G G G P P A K Q R D L E | 53219 |
| 61 | L R R G F S D S G G - P P A K Q R D L E | GI 1684847 |
| 61 | L R R G F S D S G G G P P A K Q R D L E | GI 1684843 |
| 81 | G A V S R L G G E R R T R R E S R Q E S | 53219 |
| 80 | G A V S R L G G E R R T R R E S R Q E S | GI 1684847 |
| 81 | G A V S R L G G E R R T R R E S R Q E S | GI 1684843 |
| 101 | D P E D D D V K K P A L Q S S V V A T S | 53219 |
| 100 | D P E D D D V K K P A L Q S S V V A T S | GI 1684847 |
| 101 | D P E D D D V K K P A L Q S S V V A T S | GI 1684843 |
| 121 | K E R - T R R D L I Q D Q N M D E K G K | 53219 |
| 120 | K E R - T R R D L I Q D Q N M D E K G K | GI 1684847 |
| 121 | K E R S T E R P L F Q D Q N T D E K E T | GI 1684843 |
| 140 | - Q R N R R I F G L L M G T L Q K F K Q | 53219 |
| 139 | - Q R N R R I F G L L M G T L Q K F K Q | GI 1684847 |
| 141 | P E R P G P I F G L L M G T L Q K F K Q | GI 1684843 |
| 159 | E S T V A T E R Q K R R Q E I E Q K L E | 53219 |
| 158 | E S T V A T E R Q N R R Q E I E Q K L E | GI 1684847 |
| 161 | E S T V A T E R Q K R R Q E I E Q K L E | GI 1684843 |

FIGURE 2A

| | | |
|---|---|---|
| 179 | V Q A E E E R K Q V E N E R R E L F E E | 53219 |
| 178 | V Q A E E E R K Q V E N E R R E L F E E | GI 1684847 |
| 181 | V Q A E E E R K Q V E N E R R E L F E E | GI 1684843 |
| | | |
| 199 | R R A K Q T E L R L L E Q K V E L A Q L | 53219 |
| 198 | R R A K Q T E L R L L E Q K V E L A Q L | GI 1684847 |
| 201 | R R A K Q T E L R L L E Q K V E L A Q L | GI 1684843 |
| | | |
| 219 | Q E E W N E H N A K I I K Y I R T K T K | 53219 |
| 218 | Q E E W N E H N A K I I K Y I R T K T K | GI 1684847 |
| 221 | Q E E W N E H N A K I I K Y I R T K T K | GI 1684843 |
| | | |
| 239 | P H L F Y I P G R M C P A T Q K L I E E | 53219 |
| 238 | P H L F Y I P G R M C P A T Q K L I E E | GI 1684847 |
| 241 | P H L F Y I P G R M C P A P - K L I E E | GI 1684843 |
| | | |
| 259 | S Q R K M N A L F E G R R I E F A E Q I | 53219 |
| 258 | S Q R K M N A L F D G R R I E F A E Q I | GI 1684847 |
| 260 | S Q R K T N A L F E G R R I E F A E Q I | GI 1684843 |
| | | |
| 279 | N K M E A R P R R Q S M K E K E H Q V V | 53219 |
| 278 | N K M E A R P R R Q S M K E K E H Q V V | GI 1684847 |
| 280 | N K M E A R P R R Q S M K E K E H Q V V | GI 1684843 |
| | | |
| 299 | - R N E E Q K A E Q E E G K V A Q R E E | 53219 |
| 298 | - R N E E H K A E Q E E G K V A Q R E E | GI 1684847 |
| 300 | V R N E E Q K S E Q E E G K V A P R T R | GI 1684843 |
| | | |
| 318 | E L E E T G N Q H - - - - - N D V E I E | 53219 |
| 317 | E L V E T G N Q H - - - - - N D V E I E | GI 1684847 |
| 320 | V M L R A L D D L V A R V G T P S P R R | GI 1684843 |
| | | |
| 333 | E A G E E E E K E I A I V H S D A E K E | 53219 |
| 332 | E A G E E E E K E I G I V H S D A E K E | GI 1684847 |
| 340 | G S G E E E E K E I P I V H S D A E K E | GI 1684843 |

FIGURE 2B

| | | | | | | | | | | | | | | | | | | | |
|---|---|---|---|---|---|---|---|---|---|---|---|---|---|---|---|---|---|---|---|
|353|Q|E|E|E|E|Q|K|Q|E|M|E|V|K|M|E|E|E|T|E|V| 53219
|352|Q|E|E|E|E|Q|K|Q|E|M|E|V|K|M|E|E|E|T|E|V| GI 1684847
|360|Q|E|E|E|E|Q|K|Q|E|M|E|V|K|M|E|E|E|T|E|V| GI 1684843

|373|R|E|S|E|K|Q|Q|D|S|Q|P|E|E|V|M|D|V|L|E|M| 53219
|372|R|E|S|E|K|Q|Q|D|S|Q|P|E|E|V|M|D|V|L|E|M| GI 1684847
|380|R|E|S|E|K|Q|Q|D|S|Q|P|E|E|V|M|D|V|L|E|M| GI 1684843

|393|V|E|N|V|K|H|V|I|A|D|Q|E|V|M|E|T|N|R|V|E| 53219
|392|V|E|N|V|K|H|V|I|A|D|Q|E|V|M|E|T|N|R|V|E| GI 1684847
|400|V|E|S|V|K|N|V|I|A|E|Q|E|V|M|E|T|N|Q|V|E| GI 1684843

|413|S|V|E|P|S|E|N|E|A|S|K|E|L|E|P|E|M|E|F|E| 53219
|412|S|V|E|P|S|E|N|E|A|S|K|E|L|E|P|E|M|E|F|E| GI 1684847
|420|R|V|E|P|S|E|N|E|A|S|K|E|L|E|P|E|M|E|F|E| GI 1684843

|433|I|E|P|D|K|E|C|K|S|L|S|P|G|K|E|N|V|S|A|L| 53219
|432|I|E|P|D|K|E|C|K|S|L|S|P|G|K|E|N|V|S|A|L| GI 1684847
|440|I|E|P|D|K|E|C|K|S|L|S|P|G|K|E|N|A|S|T|L| GI 1684843

|453|D|M|E|K|E|S|E|E|K|E|E|K|E|S|E|P|Q|P|E|P| 53219
|452|D|M|E|K|E|S|D|E|K|E|E|K|E|S|E|P|Q|P|E|P| GI 1684847
|460|E|M|E|N|E|P|E|E|K|E|E|K|E|S|E|P|Q|P|E|P| GI 1684843

|473|V|A|Q|P|Q|P|Q|S|Q|P|Q|L|Q|L|Q|S|Q|S|Q|P| 53219
|472|V|A|Q|P|Q|A|Q|S|Q|P|Q|L|Q|L|Q|S|Q|S|E|P| GI 1684847
|480|M|A|Q|P|Q|A|Q|S|L|P|Q|P|Q|P|Q|R|H|R|Q|S| GI 1684843

|493|-|-|-|-|-|-|-|-|-|-|-|-|-|-|-|-|-|-|-|-| 53219
|492|Q|P|Q|L|Q|P|E|P|A|Q|P|Q|L|Q|S|Q|P|Q|L|Q| GI 1684847
|500|Q|S|Q|P|Q|Q|Y|S|S|P|P|P|L|-|-|-|-|-|-|-| GI 1684843

|493|-|-|-|-|-|-|-|V|L|Q|S|Q|P|P|S|Q|P|E|D|L| 53219
|512|L|Q|S|Q|C|H|A|V|L|Q|S|H|P|P|S|Q|P|E|D|L| GI 1684847
|513|-|-|-|-|-|-|-|-|-|-|-|-|-|-|S|Q|P|E|T|L| GI 1684843

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 717 amino acids
      (B) TYPE: amino acid
      (C) STRANDEDNESS: single
      (D) TOPOLOGY: linear (vii) IMMEDIATE SOURCE:
      (A) LIBRARY: FIBRNOT01
      (B) CLONE: 53219

(xi) SEQUENCE DESCRIPTION: SEQ ID NO:1:

Met Ala Val Ala Val Arg Thr Leu Gln Glu Gln Leu Glu Lys Ala Lys
1             5               10              15

```
Glu Ser Leu Lys Asn Val Asp Glu Asn Ile Arg Lys Leu Thr Gly Arg
             20                  25                  30

Asp Pro Asn Asp Val Arg Pro Ile Gln Ala Arg Leu Leu Ala Leu Ser
         35                  40                  45

Gly Pro Gly Gly Gly Arg Gly Arg Gly Ser Leu Leu Leu Arg Arg Gly
     50                  55                  60

Phe Ser Asp Ser Gly Gly Pro Pro Ala Lys Gln Arg Asp Leu Glu
65                  70                  75                  80

Gly Ala Val Ser Arg Leu Gly Gly Glu Arg Arg Thr Arg Arg Glu Ser
             85                  90                  95

Arg Gln Glu Ser Asp Pro Glu Asp Asp Val Lys Lys Pro Ala Leu
            100                 105                 110

Gln Ser Ser Val Val Ala Thr Ser Lys Glu Arg Thr Arg Arg Asp Leu
            115                 120                 125

Ile Gln Asp Gln Asn Met Asp Glu Lys Gly Lys Gln Arg Asn Arg Arg
            130                 135                 140

Ile Phe Gly Leu Leu Met Gly Thr Leu Gln Lys Phe Lys Gln Glu Ser
145                 150                 155                 160

Thr Val Ala Thr Glu Arg Gln Lys Arg Arg Gln Glu Ile Glu Gln Lys
            165                 170                 175

Leu Glu Val Gln Ala Glu Glu Arg Lys Gln Val Glu Asn Glu Arg
            180                 185                 190

Arg Glu Leu Phe Glu Glu Arg Arg Ala Lys Gln Thr Glu Leu Arg Leu
            195                 200                 205

Leu Glu Gln Lys Val Glu Leu Ala Gln Leu Gln Glu Glu Trp Asn Glu
            210                 215                 220

His Asn Ala Lys Ile Ile Lys Tyr Ile Arg Thr Lys Thr Lys Pro His
225                 230                 235                 240

Leu Phe Tyr Ile Pro Gly Arg Met Cys Pro Ala Thr Gln Lys Leu Ile
            245                 250                 255

Glu Glu Ser Gln Arg Lys Met Asn Ala Leu Phe Glu Gly Arg Arg Ile
            260                 265                 270

Glu Phe Ala Glu Gln Ile Asn Lys Met Glu Ala Arg Pro Arg Arg Gln
            275                 280                 285

Ser Met Lys Glu Lys Glu His Gln Val Val Arg Asn Glu Glu Gln Lys
            290                 295                 300

Ala Glu Gln Glu Glu Gly Lys Val Ala Gln Arg Glu Glu Leu Glu
305                 310                 315                 320

Glu Thr Gly Asn Gln His Asn Asp Val Glu Ile Glu Glu Ala Gly Glu
            325                 330                 335

Glu Glu Glu Lys Glu Ile Ala Ile Val His Ser Asp Ala Glu Lys Glu
            340                 345                 350

Gln Glu Glu Glu Gln Lys Gln Glu Met Glu Val Lys Met Glu Glu
            355                 360                 365

Glu Thr Glu Val Arg Glu Ser Glu Lys Gln Gln Asp Ser Gln Pro Glu
            370                 375                 380

Glu Val Met Asp Val Leu Glu Met Val Glu Asn Val Lys His Val Ile
385                 390                 395                 400

Ala Asp Gln Glu Val Met Glu Thr Asn Arg Val Glu Ser Val Glu Pro
            405                 410                 415

Ser Glu Asn Glu Ala Ser Lys Glu Leu Glu Pro Glu Met Glu Phe Glu
            420                 425                 430
```

```
Ile Glu Pro Asp Lys Glu Cys Lys Ser Leu Ser Pro Gly Lys Glu Asn
    435                 440                 445

Val Ser Ala Leu Asp Met Glu Lys Glu Ser Glu Glu Lys Glu Lys
    450                 455                 460

Glu Ser Glu Pro Gln Pro Glu Pro Val Ala Gln Pro Gln Pro Gln Ser
465                 470                 475                 480

Gln Pro Gln Leu Gln Leu Gln Ser Gln Ser Gln Pro Val Leu Gln Ser
                485                 490                 495

Gln Pro Pro Ser Gln Pro Glu Asp Leu Ser Leu Ala Val Leu Gln Pro
            500                 505                 510

Thr Pro Gln Val Thr Gln Glu Gln Gly His Leu Leu Pro Glu Arg Lys
        515                 520                 525

Asp Phe Pro Val Glu Ser Val Lys Leu Thr Glu Val Pro Val Glu Pro
    530                 535                 540

Val Leu Thr Val His Pro Glu Ser Lys Ser Lys Thr Lys Thr Arg Ser
545                 550                 555                 560

Arg Ser Arg Gly Arg Ala Arg Asn Lys Thr Ser Lys Ser Arg Ser Arg
                565                 570                 575

Ser Ser Ser Ser Ser Ser Ser Ser Ser Thr Ser Ser Ser Ser
            580                 585                 590

Gly Ser Ser Ser Ser Gly Ser Ser Ser Arg Ser Ser Ser Ser
            595                 600                 605

Ser Ser Ser Ser Thr Gly Gly Ser Ser Arg Asp Ser Ser Ser Ser
    610                 615                 620

Thr Ser Ser Ser Ser Glu Ser Arg Ser Arg Ser Arg Gly Arg Gly His
625                 630                 635                 640

Asn Arg Asp Arg Lys His Arg Arg Ser Val Asp Arg Lys Arg Arg Asp
                645                 650                 655

Thr Ser Gly Leu Glu Arg Ser His Lys Ser Ser Lys Gly Gly Ser Ser
            660                 665                 670

Arg Asp Thr Lys Gly Ser Lys Asp Lys Asn Ser Arg Ser Asp Arg Lys
    675                 680                 685

Arg Ser Ile Ser Glu Ser Ser Arg Ser Gly Lys Arg Ser Ser Arg Ser
    690                 695                 700

Glu Arg Asp Arg Lys Ser Asp Arg Lys Asp Lys Arg Arg
705                 710                 715

(2) INFORMATION FOR SEQ ID NO:2:

(i) SEQUENCE CHARACTERISTICS:
        (A) LENGTH: 2369 base pairs
        (B) TYPE: nucleic acid
        (C) STRANDEDNESS: single
        (D) TOPOLOGY: linear (vii) IMMEDIATE SOURCE:
        (A) LIBRARY: FIBRNOT01
        (B) CLONE: 53219

(xi) SEQUENCE DESCRIPTION: SEQ ID NO:2:

TCTCAAGCCT GCCGCAGGGA GAAGATGGCG GTCGCCGTGA GAACTTTGCA GGAACAGCTG      60

GAAAAGGCCA AAGAGAGTCT TAAGAACGTG GATGAGAACA TTCGCAAGCT CACCGGGCGG     120

GATCCGAATG ACGTGAGGCC CATCCAAGCC AGATTGCTGG CCCTTTCTGG TCCTGGTGGA     180

GGTAGAGGAC GTGGTAGTTT ATTACTGAGG CGTGGATTCT CAGATAGTGG AGGAGGACCC     240

CCAGCCAAAC AGAGAGACCT TGAAGGGGCA GTCAGTAGGC TGGGCGGGGA GCGTCGGACC     300
```

-continued

```
AGAAGAGAAT CACGCCAGGA AAGCGACCCG GAGGATGATG ATGTTAAAAA GCCAGCATTG      360

CAGTCTTCAG TTGTAGCTAC CTCCAAAGAG CGCACACGTA GAGACCTTAT CCAGGATCAA      420

AATATGGATG AAAAGGGAAA GCAAAGGAAC CGGCGAATAT TTGGCTTGTT GATGGGTACC      480

CTTCAAAAAT TTAAACAAGA ATCCACTGTT GCTACTGAAA GGCAAAAGCG GCGCCAGGAA      540

ATTGAACAAA AACTTGAAGT TCAGGCAGAA GAAGAGAGAA AGCAGGTTGA AAATGAAAGG      600

AGAGAACTGT TGAAGAGAG GCGTGCTAAA CAGACAGAAC TGCGGCTTTT GGAACAGAAA       660

GTTGAGCTTG CGCAGCTGCA AGAAGAATGG AATGAACATA ATGCCAAAAT AATTAAATAT      720

ATAAGAACTA AGACAAAGCC CCATTTGTTT TATATTCCTG GAAGAATGTG TCCAGCTACC      780

CAAAAACTAA TAGAAGAGTC ACAGAGAAAA ATGAACGCTT TATTTGAAGG TAGACGCATC      840

GAATTTGCAG AACAAATAAA TAAAATGGAG GCTAGGCCTA GAAGACAATC AATGAAGGAA      900

AAAGAGCATC AGGTGGTGCG TAATGAAGAA CAGAAGGCGG AACAAGAAGA GGGTAAGGTG      960

GCTCAGCGAG AGGAAGAGTT GGAGGAGACA GGTAATCAGC ACAATGATGT AGAAATAGAG     1020

GAAGCAGGAG AGGAAGAGGA AAAGGAAATA GCGATTGTTC ATAGTGATGC AGAGAAAGAA     1080

CAGGAGGAGG AAGAACAAAA ACAGGAAATG GAGGTTAAGA TGGAGGAGGA AACTGAGGTA     1140

AGGGAAAGTG AGAAGCAGCA GGATAGTCAG CCTGAAGAAG TTATGGATGT GCTAGAGATG     1200

GTTGAGAATG TCAAACATGT AATTGCTGAC CAGGAGGTAA TGGAAACTAA TCGAGTTGAA     1260

AGTGTAGAAC CTTCAGAAAA TGAAGCTAGC AAAGAATTGG AACCAGAAAT GGAATTTGAA     1320

ATTGAGCCAG ATAAAGAATG TAAATCCCTT TCTCCTGGGA AAGAGAATGT CAGTGCTTTA     1380

GACATGGAAA AGGAGTCTGA GGAAAAAGAA GAAAAAGAAT CTGAGCCCCA ACCTGAGCCT     1440

GTGGCTCAAC CTCAGCCTCA GTCTCAGCCC CAGCTTCAGC TTCAATCCCA GTCCCAACCA     1500

GTACTCCAGT CCCAGCCTCC CTCTCAGCCT GAGGATTTGT CATTAGCTGT TTTACAGCCA     1560

ACACCCCAAG TTACTCAGGA GCAAGGGCAT TTACTACCTG AGAGGAAGGA TTTTCCTGTA     1620

GAGTCTGTAA AACTCACTGA GGTACCAGTA GAGCCAGTCT TGACAGTACA TCCAGAGAGC     1680

AAGAGCAAAA CCAAAACTAG GAGCAGAAGT AGAGGTCGAG CTAGAAATAA AACAAGCAAG     1740

AGTAGAAGTC GAAGCAGTAG CAGTAGCAGT TCTAGTAGCA GTTCAACCAG TAGCAGCAGT     1800

GGAAGTAGTT CCAGCAGTGG AAGTAGTAGC AGTCGCAGTA GTTCCAGTAG CAGCTCCAGT     1860

ACAGGTGGCA GCAGCAGCAG AGATAGTAGC AGTAGCACTA GTAGTAGTAG TGAGAGTAGA     1920

AGTCGGAGTA GGGGCCGGGG ACATAATAGA GATAGAAAGC ACAGAAGGAG CGTGGATCGG     1980

AAGAGAAGGG ATACTTCAGG ACTAGAAAGA AGTCACAAAT CTTCAAAAGG TGGTAGTAGT     2040

AGAGATACAA AAGGATCAAA GGATAAGAAT TCCCGGTCCG ACAGAAAGAG GTCTATATCA     2100

GAGAGTAGTC GATCAGGCAA AAGATCTTCA AGAAGTGAAA GAGACCGAAA ATCAGACAGG     2160

AAAGACAAAA GGCGTTAATG GAAGAAGCCA GGCTTTCTTA GCCATTCTTT GCAGCAGAAG     2220

ATTTCTTGAT AAAAAGGAT TACCTTTCCT TGTAAAGAGG ATGCTGCCTT AAGAATTGCA      2280

TGTTGTAAAA AATCTTTTTG GAAAATACAG ACTGTTTGTT TACCAGACAT TCTTGTACTT     2340

TTTGCATAAT TTTGTAAGAG TTATTTATC                                       2369
```

(2) INFORMATION FOR SEQ ID NO:3:

(i) SEQUENCE CHARACTERISTICS:
        (A) LENGTH: 743 amino acids
        (B) TYPE: amino acid
        (C) STRANDEDNESS: single
        (D) TOPOLOGY: linear (vii) IMMEDIATE SOURCE:
    (A) LIBRARY: GenBank
    (B) CLONE: 1684847

(xi) SEQUENCE DESCRIPTION: SEQ ID NO:3:

```
Met Ala Val Ala Val Arg Thr Leu Gln Glu Gln Leu Glu Lys Ala Lys
 1               5                  10                  15

Glu Ser Leu Lys Asn Val Asp Glu Asn Ile Arg Lys Leu Thr Gly Arg
            20                  25                  30

Asp Pro Asn Asp Val Arg Pro Ile Gln Ala Arg Leu Leu Ala Leu Ser
        35                  40                  45

Gly Pro Gly Gly Gly Arg Gly Arg Gly Ser Leu Leu Leu Arg Arg Gly
    50                  55                  60

Phe Ser Asp Ser Gly Gly Pro Pro Ala Lys Gln Arg Asp Leu Glu Gly
65                  70                  75                  80

Ala Val Ser Arg Leu Gly Gly Glu Arg Arg Thr Arg Glu Ser Arg
                85                  90                  95

Gln Glu Ser Asp Pro Glu Asp Asp Val Lys Lys Pro Ala Leu Gln
                100                 105                 110

Ser Ser Val Val Ala Thr Ser Lys Glu Arg Thr Arg Arg Asp Leu Ile
            115                 120                 125

Gln Asp Gln Asn Met Asp Glu Lys Gly Lys Gln Arg Asn Arg Arg Ile
130                 135                 140

Phe Gly Leu Leu Met Gly Thr Leu Gln Lys Phe Lys Gln Glu Ser Thr
145                 150                 155                 160

Val Ala Thr Glu Arg Gln Asn Arg Arg Gln Glu Ile Glu Gln Lys Leu
                165                 170                 175

Glu Val Gln Ala Glu Glu Arg Lys Gln Val Glu Asn Glu Arg Arg
                180                 185                 190

Glu Leu Phe Glu Glu Arg Arg Ala Lys Gln Thr Glu Leu Arg Leu Leu
            195                 200                 205

Glu Gln Lys Val Glu Leu Ala Gln Leu Gln Glu Glu Trp Asn Glu His
        210                 215                 220

Asn Ala Lys Ile Ile Lys Tyr Ile Arg Thr Lys Thr Lys Pro His Leu
225                 230                 235                 240

Phe Tyr Ile Pro Gly Arg Met Cys Pro Ala Thr Gln Lys Leu Ile Glu
                245                 250                 255

Glu Ser Gln Arg Lys Met Asn Ala Leu Phe Asp Gly Arg Arg Ile Glu
            260                 265                 270

Phe Ala Glu Gln Ile Asn Lys Met Glu Ala Arg Pro Arg Arg Gln Ser
        275                 280                 285

Met Lys Glu Lys Glu His Gln Val Val Arg Asn Glu Glu His Lys Ala
290                 295                 300

Glu Gln Glu Glu Gly Lys Val Ala Gln Arg Glu Glu Leu Val Glu
305                 310                 315                 320

Thr Gly Asn Gln His Asn Asp Val Glu Ile Glu Ala Gly Glu Glu
                325                 330                 335

Glu Glu Lys Glu Ile Gly Ile Val His Ser Asp Ala Glu Lys Glu Gln
            340                 345                 350

Glu Glu Glu Glu Gln Lys Gln Glu Met Glu Val Lys Met Glu Glu Glu
        355                 360                 365

Thr Glu Val Arg Glu Ser Glu Lys Gln Gln Asp Ser Gln Pro Glu Glu
    370                 375                 380

Val Met Asp Val Leu Glu Met Val Glu Asn Val Lys His Val Ile Ala
```

```
                                    385                 390                 395                 400
Asp Gln Glu Val Met Glu Thr Asn Arg Val Glu Ser Val Glu Pro Ser
                405                 410                 415

Glu Asn Glu Ala Ser Lys Glu Leu Pro Glu Met Glu Phe Glu Ile
            420                 425                 430

Glu Pro Asp Lys Glu Cys Lys Ser Leu Ser Pro Gly Lys Glu Asn Val
            435                 440                 445

Ser Ala Leu Asp Met Glu Lys Glu Ser Asp Glu Lys Glu Lys Glu
        450                 455                 460

Ser Glu Pro Gln Pro Glu Pro Val Ala Gln Pro Gln Ala Gln Ser Gln
465                 470                 475                 480

Pro Gln Leu Gln Leu Gln Ser Gln Ser Glu Pro Gln Pro Gln Leu Gln
                485                 490                 495

Pro Glu Pro Ala Gln Pro Gln Leu Gln Ser Gln Pro Gln Leu Gln Leu
                500                 505                 510

Gln Ser Gln Cys His Ala Val Leu Gln Ser His Pro Pro Ser Gln Pro
        515                 520                 525

Glu Asp Leu Ser Leu Ala Val Leu Gln Pro Thr Pro Gln Val Thr Gln
        530                 535                 540

Glu His Gly His Phe Leu Pro Glu Arg Lys Asp Phe Pro Val Glu Ser
545                 550                 555                 560

Val Lys Leu Thr Glu Val Pro Val Asp Pro Val Leu Thr Val His Pro
                565                 570                 575

Glu Ser Glu Ser Glu Thr Asn Thr Arg Ser Arg Ser Arg Gly Arg Thr
                580                 585                 590

Arg Asn Arg Thr Thr Lys Ser Arg Ser Arg Ser Ser Ser Ser Ser Ser
            595                 600                 605

Ser Ser Ser Ser Ser Thr Ser Ser Ser Ser Gly Ser Ser Ser Ser Ser
        610                 615                 620

Gly Ser Ser Ser Ser Arg Ser Ser Ser Ser Ser Ser Ser Thr Ser
625                 630                 635                 640

Gly Ser Ser Ser Arg Asp Ser Ser Ser Thr Ser Ser Ser Ser Glu
                645                 650                 655

Ser Arg Ser Arg Ser Arg Gly Arg Gly His Asn Arg Asp Arg Lys His
            660                 665                 670

Arg Arg Ser Val Asp Arg Lys Arg Asp Thr Ser Gly Leu Glu Arg
        675                 680                 685

Ser His Lys Ser Ser Lys Gly Gly Ser Ser Arg Asp Thr Lys Gly Ser
        690                 695                 700

Lys Asp Lys Asn Ser Arg Ser Asp Arg Lys Arg Ser Ile Ser Glu Ser
705                 710                 715                 720

Ser Arg Ser Gly Lys Arg Ser Ser Arg Ser Glu Arg Asp Arg Lys Ser
                725                 730                 735

Asp Arg Lys Asp Lys Arg Arg
            740

(2) INFORMATION FOR SEQ ID NO:4:

(i) SEQUENCE CHARACTERISTICS:
        (A) LENGTH: 703 amino acids
        (B) TYPE: amino acid
        (C) STRANDEDNESS: single
        (D) TOPOLOGY: linear (vii) IMMEDIATE SOURCE:
          (A) LIBRARY: GenBank
```

(B) CLONE: 1684843

(xi) SEQUENCE DESCRIPTION: SEQ ID NO:4:

```
Met Ala Val Ala Val Arg Thr Leu Gln Glu Gln Leu Glu Lys Ala Lys
 1               5                  10                  15

Glu Ser Leu Lys Asn Val Asp Glu Asn Ile Arg Lys Leu Thr Gly Arg
            20                  25                  30

Asp Pro Asn Asp Val Arg Pro Ile Gln Ala Arg Leu Leu Ala Leu Ser
        35                  40                  45

Gly Pro Gly Gly Arg Gly Arg Gly Ser Leu Leu Leu Arg Arg Gly
    50                  55                  60

Phe Ser Asp Ser Gly Gly Gly Pro Ala Lys Gln Arg Asp Leu Glu
65                   70                  75                  80

Gly Ala Val Ser Arg Leu Gly Gly Glu Arg Arg Thr Arg Arg Glu Ser
                85                  90                  95

Arg Gln Glu Ser Asp Pro Glu Asp Asp Val Lys Lys Pro Ala Leu
            100                 105                 110

Gln Ser Ser Val Val Ala Thr Ser Lys Glu Arg Ser Thr Glu Arg Pro
        115                 120                 125

Leu Phe Gln Asp Gln Asn Thr Asp Glu Lys Glu Thr Pro Glu Arg Pro
    130                 135                 140

Gly Pro Ile Phe Gly Leu Leu Met Gly Thr Leu Gln Lys Phe Lys Gln
145                 150                 155                 160

Glu Ser Thr Val Ala Thr Glu Arg Gln Lys Arg Arg Gln Glu Ile Glu
                165                 170                 175

Gln Lys Leu Glu Val Gln Ala Glu Glu Arg Lys Gln Val Glu Asn
            180                 185                 190

Glu Arg Arg Glu Leu Phe Glu Glu Arg Ala Lys Gln Thr Glu Leu
        195                 200                 205

Arg Leu Leu Glu Gln Lys Val Glu Leu Ala Gln Leu Gln Glu Glu Trp
    210                 215                 220

Asn Glu His Asn Ala Lys Ile Ile Lys Tyr Ile Arg Thr Lys Thr Lys
225                 230                 235                 240

Pro His Leu Phe Tyr Ile Pro Gly Arg Met Cys Pro Ala Pro Lys Leu
                245                 250                 255

Ile Glu Glu Ser Gln Arg Lys Thr Asn Ala Leu Phe Glu Gly Arg Arg
            260                 265                 270

Ile Glu Phe Ala Glu Gln Ile Asn Lys Met Glu Ala Arg Pro Arg Arg
        275                 280                 285

Gln Ser Met Lys Glu Lys Glu His Gln Val Val Arg Asn Glu Glu
    290                 295                 300

Gln Lys Ser Glu Gln Glu Glu Gly Lys Val Ala Pro Arg Thr Arg Val
305                 310                 315                 320

Met Leu Arg Ala Leu Asp Asp Leu Val Ala Arg Val Gly Thr Pro Ser
                325                 330                 335

Pro Arg Arg Gly Ser Gly Glu Glu Glu Lys Glu Ile Pro Ile Val
            340                 345                 350

His Ser Asp Ala Glu Lys Glu Gln Glu Glu Gln Lys Gln Glu
        355                 360                 365

Met Glu Val Lys Met Glu Glu Glu Thr Glu Val Arg Glu Ser Glu Lys
    370                 375                 380

Gln Gln Asp Ser Gln Pro Glu Glu Val Met Asp Val Leu Glu Met Val
385                 390                 395                 400
```

-continued

```
Glu Ser Val Lys Asn Val Ile Ala Glu Gln Glu Val Met Glu Thr Asn
            405             410             415

Gln Val Glu Arg Val Glu Pro Ser Glu Asn Glu Ala Ser Lys Glu Leu
            420             425             430

Glu Pro Glu Met Glu Phe Glu Ile Glu Pro Asp Lys Glu Cys Lys Ser
            435             440             445

Leu Ser Pro Gly Lys Glu Asn Ala Ser Thr Leu Glu Met Glu Asn Glu
    450             455             460

Pro Glu Glu Lys Glu Glu Lys Glu Ser Glu Pro Gln Pro Glu Pro Met
465             470             475             480

Ala Gln Pro Gln Ala Gln Ser Leu Pro Gln Pro Gln Pro Gln Arg His
            485             490             495

Arg Gln Ser Gln Ser Gln Pro Gln Gln Tyr Ser Ser Pro Pro Pro Leu
            500             505             510

Ser Gln Pro Glu Thr Leu Pro Leu Ala Val Ser Gln Pro Pro Pro Gln
            515             520             525

Leu Ile Gln Arg Gln Gly His Leu Pro Pro Glu Arg Lys Glu Phe Leu
    530             535             540

Val Glu Ser Val Lys Leu Thr Glu Val Pro Thr Glu Pro Val Leu Thr
545             550             555             560

Val His Ser Glu Ser Lys Tyr Glu Thr Lys Thr Arg Ser Arg Ser Arg
            565             570             575

Gly Arg Ala Arg Asn Arg Thr Ser Lys Ser Arg Ser Arg Ser Ser Ser
            580             585             590

Ser Ser Ser Ser Ser Ser Ser Thr Ser Ser Ser Ser Gly Ser Ser
            595             600             605

Ser Ser Ser Gly Ser Ser Ser Ser Arg Thr Ser Ser Ser Ser Ser Ser
    610             615             620

Thr Ser Gly Ser Ser Ser Arg Asp Ser Ser Ser Ser Thr Thr Ser Ser
625             630             635             640

Ser Glu Ser Arg Ser Arg Ser Arg Gly Arg Gly His Asn Arg Asp Arg
            645             650             655

Lys His Arg Arg Ser Val Asp Arg Lys Arg Arg Asp Ala Ser Gly Leu
            660             665             670

Glu Arg Ser His Lys Ser Ala Lys Gly Gly Ser Ser Arg Asp Ala Lys
            675             680             685

Ala Val Ser Ser Ser Gly Met Pro Arg Phe Lys Pro Gly Gln Leu
    690             695             700
```

HUMAN PININ SPLICE VARIANT

FIELD OF THE INVENTION

This invention relates to nucleic acid and amino acid sequences of a human pinin splice variant and to the use of these sequences in the diagnosis, prevention, and treatment of developmental, vesicle trafficking, neoplastic, and immunological disorders.

BACKGROUND OF THE INVENTION

Gap junctions are the relatively large pores which allow free diffusion of ions across biological membranes (Finbow, M. E. et al. (1995) Bioessays 17:247–255). The desmosome (macula adherens) is a major component of the epithelial intracellular gap junctional complex. Desmosomes are intimately involved in the structural and functional integration of adjacent epithelial cells. The desmosome serves as a site of reinforcement of cell-cell adhesion as well as an anchorage point for the intermediate filament (IF) scaffold of the cell. Therefore, the desmosome is integral in epithelial cell and epithelial sheet organization. Detailed morphological, biochemical, and molecular analyses of desmosomal components have led to the identification of, and putative function for, as many as eight desmosomal proteins. These include desmoplakin, plakoglobin, and the transmembrane cadhedrin-like glycoproteins, desmoglein and desmocollin (Ouyang, P. and Sugrue, S. P. (1996) J. Cell. Biol. 135:1027–1042).

A human placental 140 kDa phosphoprotein associated with mature desmosomes, pinin, is localized to the intracellular side of the lateral epithelial cell margins near the cytoplasmic face of the desmosomal complex. Pinin further localizes to the vicinity of the IF convergence onto the desmosomes and is recruited to preformed, morphologically identifiable desmosomes. The conceptual translation product of the cDNA clone contains three unique domains: 1) an acidic domain rich in glutamic acid; 2) a glutamine-proline, glutamine-leucine repeat domain; and 3) a serine-rich domain. The serine-rich domain, flanked by numerous protein kinase recognition motif sites, suggests that the C-terminal region of pinin may serve as a substrate(s) for serine/threonine protein kinase(s). It has been postulated that phosphorylation may play an important role in cell-cell adhesion, and in IF and IF-associated protein assembly and function. Pinin may be involved in the organization and/or stabilization of the more mature or definitive desmosome-IF complex (Ouyang, P. and Sugrue, S. P. (supra)).

Pinin cDNA transfected into a human embryonic kidney cell line resulted in enhanced cell-cell adhesion. Northern blot analysis of pinin indicated tissue-specific variation in mRNA size; genomic analysis revealed the existence of a single gene for pinin, suggesting alternative splicing of mRNA. Western blot of two-dimensional gels revealed the existence of multiple isoforms of pinin with isoelectric point ranging from 5.9 to 6.4 (Ouyang, P. and Sugrue, S. P. (supra)).

A number of clinical pathologies have been associated with desmosome morphogenesis and gap junction formation. Altered desmosome morphogenesis has been observed during wound healing, in the skin from an individual with xeroderma pigmentosum, in biopsy material from patients with Alzheimer's disease, in myocytes from patients with hypertrophic cardiomyopathy, in Hailey-Hailey disease keratinocytes, and in follicular dendritic cells and keratodermas from patients with immunosuppressive disorders (Krawczyk, W. S. and Wilgram, G. F. (1973) J. Ultrastruct. Res. 45:93–101; Plotnick, H. and Lupulescu, A. (1983) J. Am. Acad. Dermatol. 9:876–882; Wegiel, J. and Wisniewski, H. M. (1994) Acta Neuropathol. (Berl.) 87:355–361; Sepp, R. et al. (1996) Heart 76:412–417; Cooley, J. E. et al. (1996) J. Invest. Dermatol. 107:877–881; Imal, Y. and Yamakawa, M. (1996) 46:807–833). In epithelial tissue from patients with a hereditary mucoepithelial dysplasia, desmosomes are apparently localized not to the cell-cell interface, but as aggregates within the cytoplasm (Witkop, C. J. et al. (1979) Am. J. Hum. Genet. 31:414–427).

Cancer cells exhibit anchorage-independence. Transformed cells have abnormal or decreased cell-cell, and/or cell-extracellular matrix attachments. Without anchorage, the transformed cell is allowed to metastasize or grow in new environments. Anchorage tends to inhibit, rather than promote, the proliferation of transformed cells. The presence of rare desmosome type intracellular junctions has been associated with chordomas of the mediatinum and with granular cell basal cell carcinoma (Suster, S. and Moran, C. A. (1995) Hum. Pathol. 26:1354–1362; Mrak, R. E. and Baker, G. F. (1987) J. Cutan. Pathol. 14:37–42).

The discovery of a new human pinin splice variant and the polynucleotides encoding it satisfies a need in the art by providing new compositions which are useful in the diagnosis, prevention and treatment of developmental, vesicle trafficking, neoplastic, and immunological disorders.

SUMMARY OF THE INVENTION

The invention features a substantially purified polypeptide, human pinin splice variant (PNIN), having the amino acid sequence shown in SEQ ID NO:1, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO:2 or variants thereof. In addition, the invention provides a polynucleotide sequence which hybridizes under stringent conditions to the polynucleotide sequence of SEQ ID NO:2. The invention also provides a polynucleotide sequence comprising the complement of SEQ ID NO:2, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding PNIN under conditions suitable for the expression of the polypeptide; and b) recovering the polypeptide from the host cell culture.

The invention also provides a pharmaceutical composition comprising a substantially purified PNIN having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising the amino acid sequence of SEQ ID NO:1.

Still further, the invention provides a purified agonist of the polypeptide of SEQ ID NO:1.

The invention also provides a method for treating or preventing a developmental disorder comprising administering to a subject in need of such treatment an effective amount of a pharmaceutical composition comprising purified PNIN.

The invention also provides a method for treating or preventing a vesicle trafficking disorder comprising administering to a subject in need of such treatment an effective amount of a pharmaceutical composition comprising purified PNIN.

The invention also provides a method for treating or preventing a neoplastic disorder comprising administering to a subject in need of such treatment an effective amount of a pharmaceutical composition comprising purified PNIN.

The invention also provides a method for treating or preventing an immunological disorder comprising administering to a subject in need of such treatment an effective amount of an antagonist to PNIN.

The invention also provides a method for detecting a polynucleotide which encodes PNIN in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding PNIN in the biological sample. In one aspect the nucleic acid material of the biological sample is amplified by the polymerase chain reaction prior to hybridization.

BRIEF DESCRIPTION OF THE FIGURES

FIGS. 1A, 1B, 1C, 1D, 1E, 1F, and 1G show the amino acid sequence (SEQ ID NO:1) and nucleic acid sequence (SEQ ID NO:2) of PNIN. The alignment was produced using MacDNASIS PRO™ software (Hitachi Software Engineering Co. Ltd. San Bruno, Calif.).

FIGS. 2A, 2B, 2C, 2D, and 2E show the amino acid sequence alignments among PNIN (53219; SEQ ID NO:1), human pinin (GI 1684847; SEQ ID NO:3), and bovine pinin (GI 1684843; SEQ ID NO:4) produced using the multisequence alignment program of DNASTAR™ software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

PNIN, as used herein, refers to the amino acid sequences of substantially purified PNIN obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to PNIN, increases or prolongs the duration of the effect of PNIN. Agonists may include proteins, nucleic acids, carbohydrates, or any other molecules which bind to and modulate the effect of PNIN.

An "allele" or "allelic sequence", as used herein, is an alternative form of the gene encoding PNIN. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding PNIN as used herein include those with deletions, insertions, or substitutions of different nucleotides resulting in a polynucleotide that encodes the same or a functionally equivalent PNIN. Included within this definition are polymorphisms which may or may not be readily detectable using a particular oligonucleotide probe of the polynucleotide encoding PNIN, and improper or unexpected hybridization to alleles, with a locus other than the normal chromosomal locus for the polynucleotide sequence encoding PNIN. The encoded protein may also be "altered" and contain deletions, insertions, or substitutions of amino acid residues which produce a silent change and result in a functionally equivalent PNIN. Deliberate amino acid substitutions may be made on the basis of similarity in polarity, charge, solubility, hydrophobicity, hydrophilicity, and/or the amphipathic nature of the residues as long as the biological or immunological activity of PNIN is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to an oligopeptide, peptide, polypeptide, or protein sequence, and fragment thereof, and to naturally occurring or synthetic molecules. Fragments of PNIN are preferably about 5 to about 15 amino acids in length and retain the biological activity or the immunological activity of PNIN. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist", as used herein, refers to a molecule which, when bound to PNIN, decreases the amount or the duration of the effect of the biological or immunological activity of PNIN. Antagonists may include proteins, nucleic acids, carbohydrates, antibodies or any other molecules which decrease the effect of PNIN.

As used herein, the term "antibody" refers to intact molecules as well as fragments thereof, such as Fab, F(ab')$_2$, and Fv, which are capable of binding the epitopic determinant. Antibodies that bind PNIN polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic PNIN, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A—G—T" binds to the complementary sequence "T—C—A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding PNIN (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR™ (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW™ Fragment Assembly system, GCG, Madison, Wis.). Some sequences have been both extended and assembled to produce the consensus sequence The term "correlates with expression of a polynucleotide", as used herein, indicates that the detection of the presence of ribonucleic acid that is similar to SEQ ID NO:2 by northern analysis is indicative of the presence of mRNA encoding PNIN in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to PNIN or the encoded PNIN. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of PNIN. For example, modulation may cause an increase or a decrease in protein activity, binding characteristics, or any other biological, functional or immunological properties of PNIN.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length PNIN and fragments thereof.

The term "sample", as used herein, is used in its broadest sense. A biological sample suspected of containing nucleic acid encoding PNIN, or fragments thereof, or PNIN itself may comprise a bodily fluid, extract from a cell, chromosome, organelle, or membrane isolated from a cell, a cell, genomic DNA, RNA, or cDNA(in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of PNIN, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of a new human pinin splice variant (hereinafter referred to as "PNIN"), the polynucleotides encoding PNIN, and the use of these compositions for the diagnosis, prevention, or treatment of developmental, vesicle trafficking, neoplastic, and immunological disorders.

Nucleic acids encoding the PNIN of the present invention were first identified in Incyte Clone 53219 from the human lung fibroblast cDNA library (FIBRNOT01) using a computer search for amino acid sequence alignments. A consensus sequence, SEQ ID NO:2, was derived from the following overlapping and/or extended nucleic acid sequences: Incyte Clones 53219 (FIBRNOT01), 1696671 (COLNNOT23, 388628 (THYMNOT02), 891610 (STOMTUT), and 363211 (PROSNOT01).

In one embodiment, the invention encompasses a polypeptide comprising the amino acid sequence of SEQ ID NO:1, as shown in FIGS. 1A, 1B, 1C, 1D, 1E, 1F, and 1G. PNIN is 717 amino acids in length, has two potential glycosylation sites at residues N-448, and N-568; two potential glycosaminoglycan attachment sites at residues S-48, and S-68; six potential cAMP and cGMP protein kinase phosphorylation sites at residues T-30, S-96, S-289, T-654, S-687, and S-699; 20 potential casein kinase II phosphorylation sites at residues T-7, T-30, T-92, S-96, S-100, T-119, T-124, S-289, S-381, S-417, S-450, S-500, S-617, S-627, S-658, S-671, S-683, S-690, S-702, and S-704; and has 24 potential protein kinase C phosphorylation sites at residues S-18, T-30, T-92, T-l 19, T-124, T-164, T-252, S-259, S-289, S-375, T-408, S-534, T-570, S-602, S-617, S-663, S-666, S-671, S-685, S-694, S-697, S-701, S-704, and S-710. PNIN has an acidic domain rich in glutamic acid between E-330 and E-471; has a glutamine-leucine, glutamin-proline repeat domain between Q-475 and P-492; and has a serine-rich domain between S-576 and S-629. As shown in FIGS. 2A, 2B, 2C, 2D, and 2E, PNIN has chemical and structural homology with human pinin (GI 1684847; SEQ ID NO:3) and bovine pinin (GI 1684843; SEQ ID NO:4). In particular, PNIN and human pinin share 94% identity, share an acidic domain rich in glutamic acid, share a glutamine-leucine, glutamine-proline repeat domain, and share a serine-rich domain. PNIN has an estimated isoelectric point (pI) of 6.75 (MacDNASIS PRO software). Human pinin includes an additional 27 amino acid residues insertion between PNIN residues P-492 and V-493. Analysis of the cDNA sequence at this insertion point, C—C—A—splice—G—T—C, does not indicate a normal mRNA splice site such as A/C—A/ G—G—splice—G/U/A—U/C/G—U/G. Bovine pinin includes an additional 13 amino acid residues at the same insertion point, and has a truncated C-terminus with respect to PNIN.

Northern analysis shows the expression of this sequence in various libraries, at least 43% of which are immortalized or cancerous and at least 37% of which involve immune response. Of particular note is the expression of PNIN in fetal and proliferating tissues, and in heart, gut, and secretory tissues.

The invention also encompasses PNIN variants. A preferred PNIN variant is one having at least 80%, and more preferably at least 90%, amino acid sequence identity to the PNIN amino acid sequence (SEQ ID NO:1) and which retains at least one biological, immunological or other functional characteristic or activity of PNIN. A most preferred PNIN variant is one having at least 95% amino acid sequence identity to SEQ ID NO:1.

The invention also encompasses polynucleotides which encode PNIN. Accordingly, any nucleic acid sequence which encodes the amino acid sequence of PNIN can be used to produce recombinant molecules which express PNIN. In a particular embodiment, the invention encompasses the polynucleotide comprising the nucleic acid sequence of SEQ ID NO:2 as shown in FIGS. 1A, 1B, 1C, 1D, 1E, 1F, and 1G.

It will be appreciated by those skilled in the art that as a result of the degeneracy of the genetic code, a multitude of nucleotide sequences encoding PNIN, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring PNIN, and all such variations are to be considered as being specifically disclosed.

Although nucleotide sequences which encode PNIN and its variants are preferably capable of hybridizing to the nucleotide sequence of the naturally occurring PNIN under appropriately selected conditions of stringency, it may be advantageous to produce nucleotide sequences encoding PNIN or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding PNIN and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode PNIN and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding PNIN or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, Sequenase® (U.S. Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding PNIN may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode PNIN may be used in recombinant DNA molecules to direct expression of PNIN, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express PNIN.

As will be understood by those of skill in the art, it may be advantageous to produce PNIN-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter PNIN encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding PNIN may be ligated to a heterologous sequence to encode a fusion protein. For example, to screen peptide libraries for inhibitors of PNIN activity, it may be useful to encode a chimeric PNIN protein that can be recognized by a commercially available antibody. A fusion protein may also be engineered to contain a cleavage site located between the PNIN encoding sequence and the heterologous protein sequence, so that PNIN may be cleaved and purified away from the heterologous moiety.

In another embodiment, sequences encoding PNIN may be synthesized, in whole or in part, using chemical methods well known in the art (see Caruthers, M. H. et al. (1980) Nucl. Acids Rs. Symp. Ser. 215–223, Horn, T. et al. (1980) Nucl. Acids Rs. Symp. Ser. 215225–232). Alternatively, the protein itself may be produced using chemical methods to synthesize the amino acid sequence of PNIN, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of PNIN, or any part thereof, may be altered during direct synthesis and/or combined using chemical methods with sequences from other proteins, or any part thereof, to produce a variant polypeptide.

In order to express a biologically active PNIN, the nucleotide sequences encoding PNIN or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding PNIN and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding PNIN. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding PNIN, vectors based on SV40 or EBV may be used with an appropriate selectable marker.

In bacterial systems, a number of expression vectors may be selected depending upon the use intended for PNIN. For example, when large quantities of PNIN are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding PNIN may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding PNIN may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express PNIN. For example, in one such system, *Autographa californica* nuclear polyhedrosis virus (AcNPV) is used as a vector to express foreign genes in *Spodoptera frugiperda* cells or in Trichoplusia larvae. The sequences encoding PNIN may be cloned into a non-essential region of the virus, such as the polyhedrin gene, and placed under control of the polyhedrin promoter. Successful insertion of PNIN will render the polyhedrin gene inactive and produce recombinant virus lacking coat protein. The recombinant viruses may then be used to infect, for example, *S. frugiperda* cells or Trichoplusia larvae in which PNIN may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding PNIN may be ligated into an adenovirus transcription/translation complex consisting of the late promoter and tripartite leader sequence. Insertion in a non-essential E1 or E3 region of the viral genome may be used to obtain a viable virus which is capable of expressing PNIN in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding PNIN. Such signals include the ATG initiation codon and adjacent sequences. In cases where sequences encoding PNIN, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-tern, high-yield production of recombinant proteins, stable expression is preferred. For example, cell lines which stably express PNIN may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding PNIN is inserted within a marker gene sequence, transformed cells containing sequences encoding PNIN can be identified by the absence of marker gene function. Alternatively, a marker gene can be placed in tandem with a sequence encoding PNIN under the control of a single promoter. Expression of the marker gene in response to induction or selection usually indicates expression of the tandem gene as well.

Alternatively, host cells which contain the nucleic acid sequence encoding PNIN and express PNIN may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding PNIN can be detected by DNA-DNA or DNA-RNA hybridization or amplification using probes or fragments or fragments of polynucleotides encoding PNIN. Nucleic acid amplification based assays involve the use of oligonucleotides or oligomers based on the sequences encoding PNIN to detect transformants containing DNA or RNA encoding PNIN.

A variety of protocols for detecting and measuring the expression of PNIN, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on PNIN is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding PNIN include oligolabeling, nick translation, end-labeling or PCR amplification using a labeled nucleotide. Alternatively, the sequences encoding PNIN, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding PNIN may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode PNIN may be designed to contain signal sequences which direct secretion of PNIN through a prokaryotic or eukaryotic cell membrane. Other constructions may be used to join sequences encoding PNIN to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and PNIN may be used to facilitate purification. One such expression vector provides for expression of a fusion protein containing PNIN and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying PNIN from the fusion protein. A discussion of vectors which contain fusion proteins is provided in Kroll, D. J. et al. (1993; DNA Cell Biol. 12:441–453).

In addition to recombinant production, fragments of PNIN may be produced by direct peptide synthesis using solid-phase techniques Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of PNIN may be chemically synthesized separately and combined using chemical methods to produce the full length molecule.

Therapeutics

Chemical and structural homology exists among PNIN and pinins from human placenta (GI 1684847) and bovine kidney cells (GI 1684843). In addition, PNIN is expressed in immortalized or cancerous tissue; in inflammatory tissue; in fetal and proliferating tissues; and in heart, gut, and secretory tissues. Therefore, PNIN appears to play a role in developmental, vesicle trafficking, neoplastic, and immunological disorders.

Therefore, in one embodiment, PNIN or a fragment or derivative thereof may be administered to a subject to treat a developmental disorder. The term "developmental disorder" refers to any disorder associated with development or function of a tissue, organ, or system of a subject, i.e., brain, adrenal gland, kidney, skeletal or reproductive system. Such disorders include, but are not limited to, renal tubular acidosis, anemia, Cushing's syndrome, achondroplastic dwarfism, epilepsy, gonadal dysgenesis, WAGR syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma, cataract, or sensorineural hearing loss.

In another embodiment, a vector capable of expressing PNIN, or a fragment or a derivative thereof, may also be administered to a subject to treat a developmental disorder including, but not limited to, those described above.

In still another embodiment, an agonist of PNIN may also be administered to a subject to treat a developmental disorder including, but not limited to, those described above.

In another embodiment, PNIN or a fragment or derivative thereof may be administered to a subject to treat a vesicle trafficking disorder. Such disorders include, but are not limited to, cystic fibrosis, glucose-galactose malabsorption syndrome, hypercholesterolemia, diabetes mellitus, diabetes insipidus, hyper- and hypoglycemia, Grave's disease, goiter, Cushing's disease, and Addison's disease; gastrointestinal disorders including ulcerative colitis, gastric and duodenal ulcers; other conditions associated with abnormal vesicle trafficking including AIDS; allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; toxic shock syndrome; traumatic tissue damage; and viral, bacterial, fungal, helminth, and protozoal infections.

In another embodiment, a vector capable of expressing PNIN, or a fragment or a derivative thereof, may also be administered to a subject to treat a vesicle trafficking disorder including, but not limited to, those listed above.

In still another embodiment, an agonist of PNIN may also be administered to a subject to treat a vesicle trafficking disorder including, but not limited to, those listed above.

In another embodiment, PNIN or a fragment or derivative thereof may be administered to a subject to treat a neoplastic disorder. Such disorders may include, but are not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing PNIN, or a fragment or a derivative thereof, may also be administered to a subject to treat a neoplastic disorder including, but not limited to, those described above.

In still another embodiment, an agonist which modulates the activity of PNIN may also be administered to a subject to treat a neoplastic disorder including, but not limited to, those described above.

In one embodiment, an antagonist of PNIN may be administered to a subject to prevent or treat an immunological disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, Werner syndrome, and autoimmune thyroiditis; complications of cancer, hemodialysis, and extracorporeal circulation; viral, bacterial, fungal, parasitic, protozoal, and helminthic infections; and trauma. In one aspect, an antibody which specifically binds RCN may be used directly as an antagonist or indirectly as a targeting or delivery mechanism for bringing a pharmaceutical agent to cells or tissue which express PNIN.

In another embodiment, a vector expressing the complement of the polynucleotide encoding PNIN may be administered to a subject to treat or prevent an immunological disorder including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of PNIN may be produced using methods which are generally known in the art. In particular, purified PNIN may be used to produce antibodies or to screen libraries of pharmaceutical agents to identify those which specifically bind PNIN.

Antibodies to PNIN may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with PNIN or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to PNIN have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of PNIN amino acids may be fused with those of another protein such as keyhole limpet hemocyanin and antibody produced against the chimeric molecule.

Monoclonal antibodies to PNIN may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce PNIN-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for PNIN may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between PNIN and its specific antibody. A two-site, monoclonal-based immunoassay utilizing monoclonal antibodies reactive to two non-interfering PNIN epitopes is preferred, but a competitive binding assay may also be employed (Maddox, supra).

In another embodiment of the invention, the polynucleotides encoding PNIN, or any fragment or complement thereof, may be used for therapeutic purposes. In one aspect, the complement of the polynucleotide encoding PNIN may be used in situations in which it would be desirable to block the transcription of the mRNA. In particular, cells may be transformed with sequences complementary to polynucleotides encoding PNIN. Thus, complementary molecules or fragments may be used to modulate PNIN activity, or to achieve regulation of gene function. Such technology is now well known in the art, and sense or antisense oligonucleotides or larger fragments, can be designed from various locations along the coding or control regions of sequences encoding PNIN.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding PNIN. These techniques are described both in Sambrook et al. (supra) and in Ausubel et al. (supra).

Genes encoding PNIN can be turned off by transforming a cell or tissue with expression vectors which express high levels of a polynucleotide or fragment thereof which encodes PNIN. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding PNIN (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding PNIN.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding PNIN. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of PNIN, antibodies to PNIN, mimetics, agonists, antagonists, or inhibitors of PNIN. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of PNIN, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example PNIN or fragments thereof, antibodies of PNIN, agonists, antagonists or inhibitors of PNIN, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind PNIN may be used for the diagnosis of conditions or diseases characterized by expression of PNIN, or in assays to monitor patients being treated with PNIN, agonists, antagonists or inhibitors. The antibodies useful for diagnostic purposes may be prepared in the same manner as those described above for therapeutics. Diagnostic assays for PNIN include methods which utilize the antibody and a label to detect PNIN in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring PNIN are known in the art and provide a basis for diagnosing altered or abnormal levels of PNIN expression. Normal or standard values for PNIN expression are established by combining body fluids or cell extracts taken from normal mammalian subjects, preferably human, with antibody to PNIN under conditions suitable for complex formation. The amount of standard complex formation may be quantified by various methods, but preferably by photometric means. Quantities of PNIN expressed in subject samples, control and disease, from biopsied tissues are compared with the standard values. Deviation between standard and subject values establishes the parameters for diagnosing disease.

In another embodiment of the invention, the polynucleotides encoding PNIN may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of PNIN may be correlated with disease. The diagnostic assay may be used to distinguish between absence, presence, and excess expression of PNIN, and to monitor regulation of PNIN levels during therapeutic intervention.

In one aspect, hybridization with PCR probes which are capable of detecting polynucleotide sequences, including genomic sequences, encoding PNIN or closely related molecules, may be used to identify nucleic acid sequences which encode PNIN. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding PNIN, alleles, or related sequences.

Probes may also be used for the detection of related sequences, and should preferably contain at least 50% of the nucleotides from any of the PNIN encoding sequences. The hybridization probes of the subject invention may be DNA or RNA and derived from the nucleotide sequence of SEQ ID NO:2 or from genomic sequence including promoter, enhancer elements, and introns of the naturally occurring PNIN.

Means for producing specific hybridization probes for DNAs encoding PNIN include the cloning of nucleic acid sequences encoding PNIN or PNIN derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding PNIN may be used for the diagnosis of conditions or disorders which are associated with expression of PNIN. Examples of such conditions or disorders include a developmental disorder such as renal tubular acidosis, anemia, Cushing's syndrome, achondroplastic dwarfism, epilepsy, gonadal dysgenesis, WAGR syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma, cataract, or sensorineural hearing loss; a vesicle trafficking disorder such as cystic fibrosis, glucose-galactose malabsorption syndrome, hypercholesterolemia, diabetes mellitus, diabetes insipidus, hyper- and hypoglycemia, Grave's disease, goiter, Cushing's disease, Addison's disease; gastrointestinal disorders including ulcerative colitis, gastric and duodenal ulcers; other conditions associated with abnormal vesicle trafficking including AIDS; allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; toxic shock syndrome; traumatic tissue damage; and viral, bacterial, fungal, helminth, and protozoal infections; a neoplastic disorder such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and an immunological disorder such as AIDS, adult respiratory distress syndrome, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, myocardial or pericardial inflammation, osteoarthritis, osteoporosis, pancreatitis, polymyositis, Werner syndrome, and autoimmune thyroiditis; complications of cancer, hemodialysis, and extracorporeal circulation; and trauma. The polynucleotide sequences encoding PNIN may be used in Southern or northern analysis, dot blot, or other membrane-based technologies; in PCR technologies; or in dipstick, pin, ELISA assays or microarrays utilizing fluids or tissues from patient biopsies to detect altered PNIN expression. Such qualitative or quantitative methods are well known in the art.

In a particular aspect, the nucleotide sequences encoding PNIN may be useful in assays that detect activation or induction of various cancers, particularly those mentioned above. The nucleotide sequences encoding PNIN may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding PNIN in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of PNIN, a normal or standard profile for expression is established. This may be accomplished by combining body fluids or cell extracts taken from normal subjects, either animal or human, with a sequence, or a fragment thereof, which encodes PNIN, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding PNIN may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of PNIN include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229-212:236). The speed of quantitation of multiple samples may be accelerated by running the assay in an ELISA format where the oligomer of interest is presented in various dilutions and a spectrophotometric or calorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14:1675–1680) and Schena, M. et al. (1996; Proc. Natl. Acad. Sci. 93:10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode PNIN may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding PNIN on a physical chromosomal map and a specific disease , or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, PNIN, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between PNIN and the agent being tested, may be measured.

Another technique for drug screening which may be used provides for high throughput screening of compounds having suitable binding affinity to the protein of interest as described in published PCT application WO84/03564. In this method, as applied to PNIN large numbers of different small test compounds are synthesized on a solid substrate, such as plastic pins or some other surface. The test compounds are reacted with PNIN, or fragments thereof, and washed. Bound PNIN is then detected by methods well known in the art. Purified PNIN can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding PNIN specifically compete with a test compound for binding PNIN. In this manner, the antibodies can be used to detect the presence of any peptide which shares one or more antigenic determinants with PNIN.

In additional embodiments, the nucleotide sequences which encode PNIN may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I FIBRNOT01 cDNA Library Construction

The W138 lung fibroblast cell line was derived from a three-month-old Caucasian female fetus. The FIBRNOT01 cDNA library was constructed at Stratagene (Cat. #937212, Stratagene). cDNA synthesis was initiated using an XhoI-oligo d(T) primer. Double stranded cDNA was blunted, ligated to EcoRI adaptors, digested with XhoI, size selected, and cloned into the XhoI and EcoRI sites of the Lambda UniZAP® vector (Stratagene). Following Lambda UniZAP packaging, $2 \times 10^6$ primary clones were then amplified to stabilize the library for long-term storage.

The quality of the cDNA library was screened using DNA probes, and then, the Bluescript® phagemid (Stratagene) was excised. Subsequently, the custom-constructed library phage particles were infected into *E. coli* host strain XL1-Blue® (Stratagene). Alternative unidirectional vectors include, but are not limited to, pcDNA1 (Invitrogen, Carlsbad, Calif.) and pSHlox-1 (Novagen, Madison Wis.).

II Isolation and Sequencing of cDNA Clones

The phagemid forms of individual cDNA clones were obtained by the in vivo excision process, in which the host bacterial strain, XPORT *E. coli* (Stratagene, XL1 Blue strain) was coinfected with both the lambda library phage (Lambda ZAP®II, Stratagene) and an f1 helper phage (Ex Assist, Stratagene). Polypeptides or enzymes derived from both the library-containing phage and the helper phage nicked the DNA, initiating new DNA synthesis from defined sequences on the target DNA and creating a smaller, single stranded circular phagemid DNA molecule that included all DNA, sequences of the pBluescript phagemid and the cDNA insert. The phagemid DNA was released from the cells and purified, then used to re-infect fresh host cells (SOLR, Stratagene) where the double stranded DNA was produced. Because the phagemid carries the gene for β-lactamase, the newly-transformed bacteria were selected on medium containing ampicillin.

Phagemid DNA was purified using QIAwell™-8 Plasmid QIAwell PLUS, or QIAwell ULTRA DNA purification system (QIAGEN, Inc., Chatsworth, Calif.). An alternative method for purifying the phagemid utilizes the Miniprep Kit available from Advanced Genetic Technologies Corp. (Gaithersburg, Md.).

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul, S. F. (1993) J. Mol. Evol. 36:290–300; Altschul et al. (1990) J. Mol. Biol. 215:403–410).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R. F. and T. F. Smith (1992; Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin, S. and S. F. Atschul (1993; Proc. Nat. Acad. Sci. 90:5873–7) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and mammalian sequences (mam), and deduced amino acid sequences from the same clones are searched against GenBank functional protein databases, mammalian (mamp), vertebrate (vrtp) and eukaryote (eukp), for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, (1993), supra: Altschul et al. (1990), supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding PNIN occurs. Abundance and percent abundance are also reported. Abundance directly reflects the number of times a particular transcript is represented in a cDNA library, and percent abundance is abundance divided by the total number of sequences examined in the cDNA library.

V Extension of PNIN Encoding Polynucleotides

The nucleic acid sequence of the Incyte Clone 53219 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent E. coli cells (in 40 μl of appropriate media) were transformed with 3 μl of ligation mixture and cultured in 80 μl of SOC medium (Sambrook et al., supra). After incubation for one hour at 37° C., the E. coli mixture was plated on Luria Bertani (LB)-agar (Sambrook et al., supra) containing 2x Carb. The following day, several colonies were randomly picked from each plate and cultured in 150 μl of liquid LB/2x Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3x) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 μCi of [$\gamma$-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). An aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the PNIN-encoding sequence, or any part thereof, is used to decrease or inhibit expression of naturally occurring PNIN. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of PNIN, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the PNIN-encoding transcript.

IX Expression of PNIN

Expression of PNIN is accomplished by subcloning the cDNAs into appropriate vectors and transforming the vectors into host cells. In this case, the cloning vector is also used to express PNIN in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of PNIN into the bacterial growth media which can be used directly in the following assay for activity.

X Demonstration of PNIN Activity

The human embryonic kidney-derived 293 cells have little or no pinin expression; purified desmosomes lacking pinin may be isolated and used to assay PNIN (Ouyang, P. and Sugrue, S. P. (supra); Franke W. W. et al. (1983) Eur. J. Cell Biol. 32:117–130). The desmosome-stabilizing ability of PNIN is assayed by monitoring its effect on transmembrane pH gradients in liposomes (Stillwell, W. and Doram, K. (1980) Biochem. Biophys. Res. Comm. 93:326–332). Purified desmosomal components are reconstituted into liposomes by sonication. The pH-sensitive fluorescent dye pyranine (Eastman Kodak) is then incorporated into the proteoliposomes by rapid freeze-thawing and sonication. Excess dye is removed by centrifugation and re-suspension of the liposomes into an appropriate buffer. PNIN is added and proton efflux is monitored by the fluorescence changes arising from changes in internal pH of the liposomes at excitation and emission wavelengths of 460 nm and 508 nm, respectively.

XI Production of PNIN Specific Antibodies

PNIN that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring PNIN Using Specific Antibodies

Naturally occurring or recombinant PNIN is substantially purified by immunoaffinity chromatography using antibodies specific for PNIN. An immunoaffinity column is constructed by covalently coupling PNIN antibody to an activated chromatographic resin, such as CNBr-activated Sepharose (Pharmacia & Upjohn). After the coupling, the resin is blocked and washed according to the manufacturer's instructions.

Media containing PNIN is passed over the immunoaffinity column, and the column is washed under conditions that allow the preferential absorbance of PNIN (e.g., high ionic strength buffers in the presence of detergent). The column is eluted under conditions that disrupt antibody/PNIN binding (eg, a buffer of pH 2–3 or a high concentration of a chaotrope, such as urea or thiocyanate ion), and PNIN is collected.

XIII Identification of Molecules Which Interact with PNIN

PNIN or biologically active fragments thereof are labeled with $^{125}$I Bolton-Hunter reagent (Bolton et al. (1973) Biochem. J. 133:529). Candidate molecules previously arrayed in the wells of a multi-well plate are incubated with the labeled PNIN, washed and any wells with labeled PNIN complex are assayed. Data obtained using different concentrations of PNIN are used to calculate values for the number, affinity, and association of PNIN with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding the human pinin splice variant of SEQ ID NO:1.

2. An isolated and purified polynucleotide sequence which is completely complementary to the polynucleotide sequence of claim 1.

3. An expression vector comprising the polynucleotide of claim 1.

4. A method for detecting a polynucleotide which encodes human pinin splice variant in a biological sample comprising the steps of:
   a) hybridizing the polynucleotide of claim 2 to nucleic acid material of a biological sample, thereby forming a hybridization complex; and
   b) detecting said hybridization complex, wherein the presence of said complex correlates with the presence of a polynucleotide encoding human pinin splice variant in said biological sample.

5. The method of claim 4 wherein the nucleic acid material is amplified by the polymerase chain reaction prior to hybridization.

6. An isolated and purified polynucleotide sequence comprising SEQ ID NO:2.

7. An isolated and purified polynucleotide sequence which is completely complementary to the polynucleotide sequence of claim 6.

8. A host cell containing the vector of claim 3.

9. A method for producing a polypeptide comprising the amino acid sequence of SEQ ID NO:1, the method comprising the steps of:
   a) culturing the host cell of claim 8 under conditions suitable for the expression of the polypeptide; and
   b) recovering the polypeptide from the host cell culture.

* * * * *